(12) United States Patent
Muldoon et al.

(10) Patent No.: US 12,005,203 B2
(45) Date of Patent: Jun. 11, 2024

(54) ARTICULATING SHAFT FOR A STEERABLE CATHETER SYSTEM AND FABRICATION METHOD

(71) Applicant: Creganna Unlimited Company, Galway (IE)

(72) Inventors: Damian Muldoon, Galway (IE); Bernard McDermott, Galway (IE)

(73) Assignee: Creganna Unlimited Company, Galway (IE)

( * ) Notice: Subject to any disclaimer, the term of this patent is extended or adjusted under 35 U.S.C. 154(b) by 600 days.

(21) Appl. No.: 17/122,565

(22) Filed: Dec. 15, 2020

(65) Prior Publication Data

US 2021/0178123 A1 Jun. 17, 2021

(30) Foreign Application Priority Data

Dec. 17, 2019 (EP) .................................... 19216804

(51) Int. Cl.
| | | |
|---|---|---|
| *A61M 25/01* | (2006.01) | |
| *B33Y 10/00* | (2015.01) | |
| *B33Y 70/00* | (2020.01) | |
| *B33Y 80/00* | (2015.01) | |

(52) U.S. Cl.
CPC .... *A61M 25/0147* (2013.01); *A61M 25/0138* (2013.01); *B33Y 10/00* (2014.12); *B33Y 70/00* (2014.12); *B33Y 80/00* (2014.12); *A61M 2207/00* (2013.01)

(58) Field of Classification Search
CPC .......... A61M 25/0147; A61M 25/0138; A61M 25/0013
See application file for complete search history.

(56) References Cited

U.S. PATENT DOCUMENTS 4,911,148 A * 3/1990 Sosnowski ......... A61B 1/00165
600/164
6,012,494 A * 1/2000 Balazs ..................... B25J 18/06
138/119

FOREIGN PATENT DOCUMENTS

| EP | 2949262 A1 * | 12/2015 | ........... A61B 1/0055 |
| EP | 2949262 A1 | 12/2015 | |
| WO | 2004105849 A1 | 12/2004 | |

OTHER PUBLICATIONS

Extended European Search Report, dated Jun. 25, 2020, 8 pages.
English translation of WO2004105849, dated Dec. 9, 2004, 17 pages.

* cited by examiner

*Primary Examiner* — Deanna K Hall
(74) *Attorney, Agent, or Firm* — Barley Snyder

(57) ABSTRACT

An articulating shaft for a steerable catheter system includes a tubular body and a plurality of wire support elements integrally formed from a single piece with the tubular body. The tubular body has a longitudinal central axis and a sealed lumen with a distal opening and a proximal opening. The wire support elements support an actuating wire. Each of the wire support elements has a feed-through opening receiving the actuating wire. A pair of adjacent wire support elements are separated from each other in an axial direction by a slot.

10 Claims, 4 Drawing Sheets

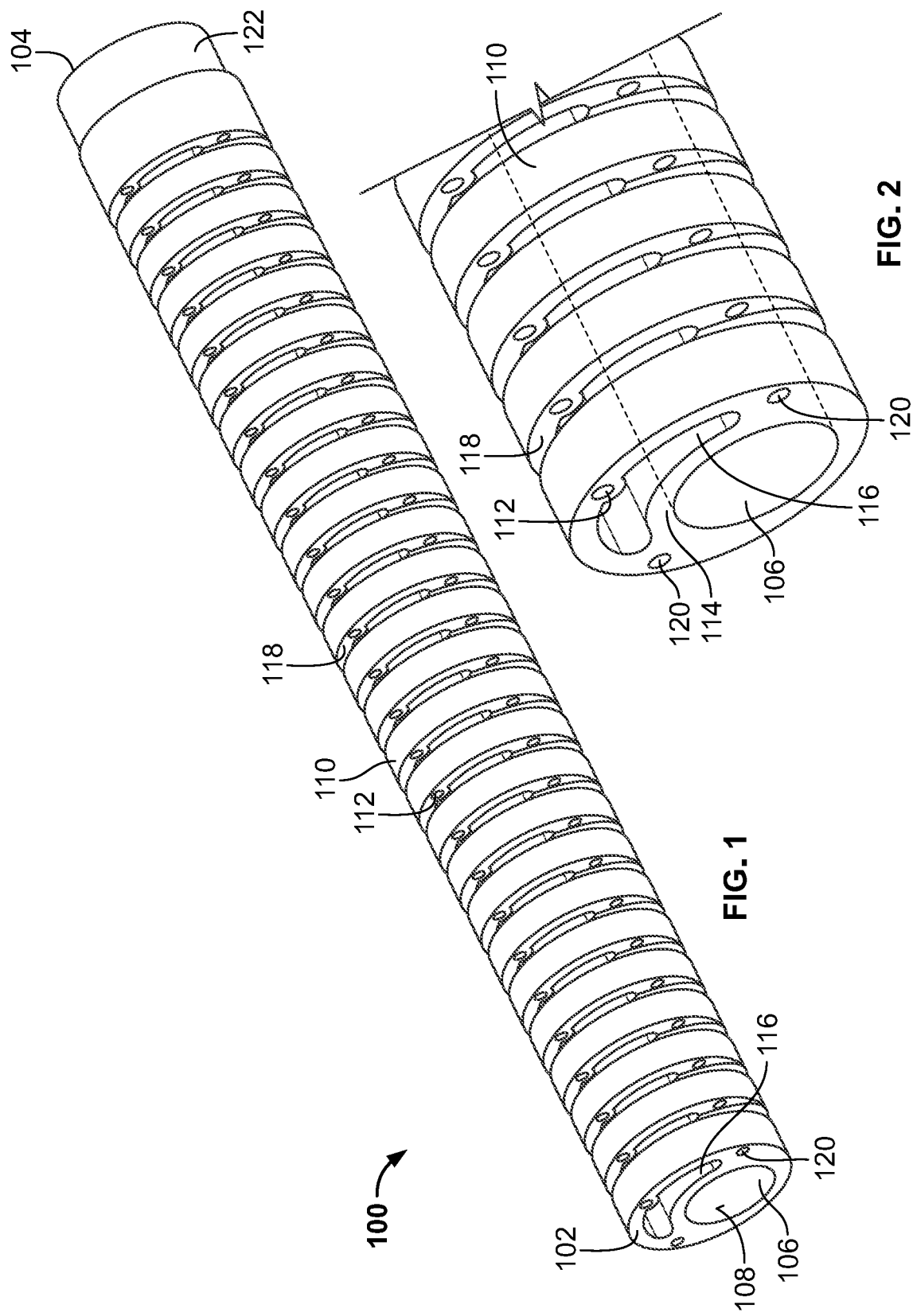

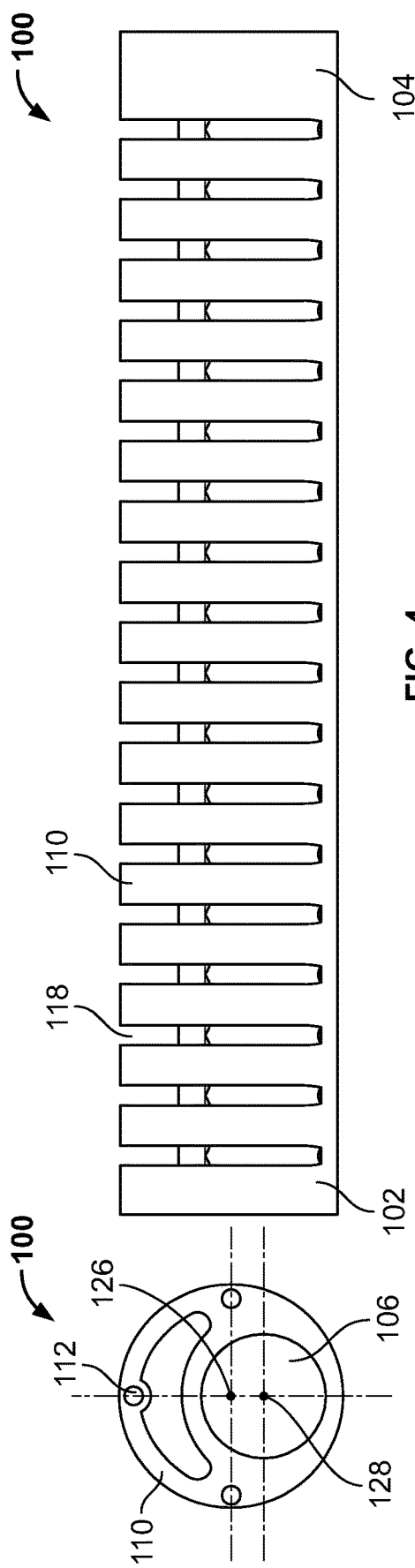

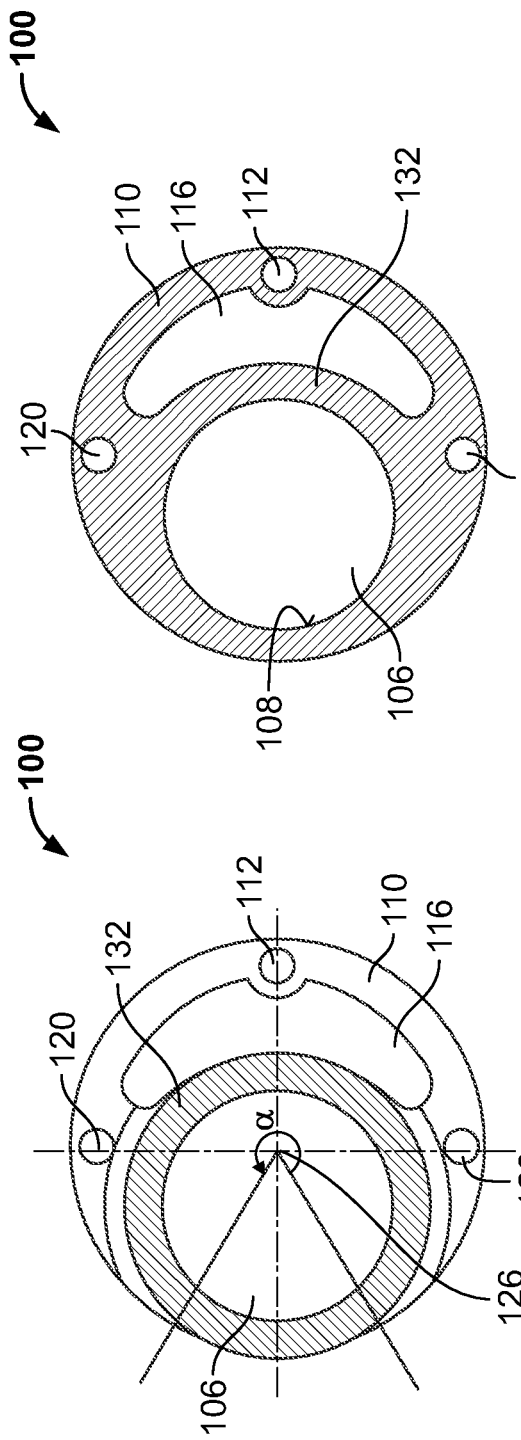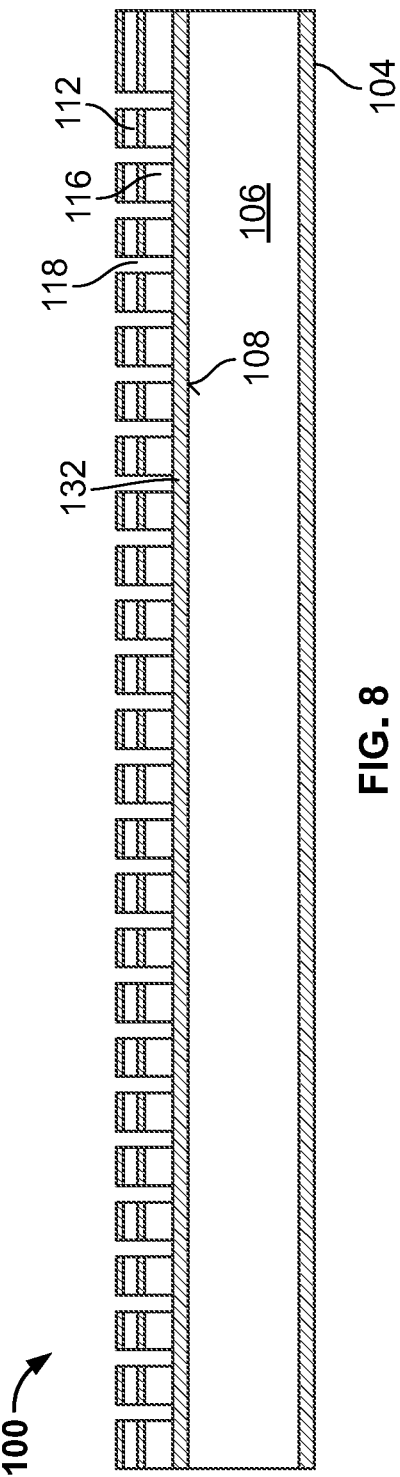

ARTICULATING SHAFT FOR A STEERABLE CATHETER SYSTEM AND FABRICATION METHOD

CROSS-REFERENCE TO RELATED APPLICATION

This application claims the benefit of the filing date under 35 U.S.C. § 119(a)-(d) of European Patent Application No. 19216804, filed on Dec. 17, 2019.

FIELD OF THE INVENTION

The present invention relates to a steerable catheter system and, more particularly, to an articulating shaft for a steerable catheter system.

BACKGROUND

Intravascular medical procedures allow the performance of therapeutic treatments in a variety of locations within a patient's body while requiring only relatively small access incisions. An intravascular procedure may, for example, eliminate the need for open-heart surgery, reducing risks, costs, and time associated with an open-heart procedure. The intravascular procedure also enables faster recovery times with lower associated costs and risks of complication.

An example of an intravascular procedure that significantly reduces procedure and recovery time and cost over conventional open surgery is a heart valve replacement or repair procedure in which an artificial valve or valve repair device is guided to the heart through the patient's vasculature. For example, a catheter is inserted into the patient's vasculature and directed to the inferior vena cava. The catheter is then urged through the inferior vena cava toward the heart by applying force longitudinally to the catheter. Upon entering the heart from the inferior vena cava, the catheter enters the right atrium. The distal end of the catheter may be deflected by one or more deflecting mechanisms, which can be achieved by a tension cable, or other mechanisms positioned inside the catheter. Precise control of the distal end of the catheter allows for more reliable and faster positioning of a medical device and/or implant and other improvements in the procedures. Apart from structural heart applications, the catheters are also used for minimally invasive procedures such as neurovascular, coronary, peripheral vascular or endoscopic type procedures for gastrointestinal applications or other.

An intravascular delivered device needs to be placed precisely to ensure a correct positioning of the medical device, which is essential for its functionality, as the device may be difficult to reposition after the device is fully deployed from the delivery system. Additionally, catheters are required to have the ability to turn or rotate the distal end of the catheter with like-for-like movement of the proximal section or catheter handle. It is achieved through torque transfer along the length of the shaft. For example, single steer to traverse an anatomical challenge. At the same time, catheters are required to achieve movement of parts of the catheter independent of the rest of the catheter. The design of the catheter shaft is a significant factor in determining the formation of curves, angles of deflection and levels of steerability. The choice of material determines the level of pushability, torque, and flexibility and it can be manipulated along the length of the catheter through a variety of means to achieve the desired results.

A catheter shaft needs to be placed precisely to ensure a correct positioning of the medical device. Multiple lumens may be created within catheters for the passage of guidewires, catheters, fluids, and gases. The number of lumens depends on the material and cross-sectional area. Lumens can be shaped to meet user requirements. Reinforcement bars (or wires) and pull wires may be inserted in the lumens. A core lumen is usually provided for receiving the catheter with the medial device. Such a core lumen needs to be sealed hermetically in order to protect the medical device.

It is known to use single or multilumen shafts and braided, coiled or other layers arranged thereon for enhanced torqueability and deflection. Reinforcement bars and pull wires may be placed in situ during the braiding process. Lack of symmetry in the braid reinforcement layers due to the presence of varying thickness of wire height lead to suboptimal and often poor torque performance through the length of the catheter shaft. Additionally, problems may occur during fabrication related to the integration of reinforcement or pull wires in the lumens, moreover, a complex braider setup has to be provided for assembling the additional braided layers, thus increasing the fabrication costs. There is still a need for an articulating shaft that has improved mechanical properties and allows the hermetic sealing of the core lumen, at the same time improving the fabrication process and reducing the costs of production.

SUMMARY

An articulating shaft for a steerable catheter system includes a tubular body and a plurality of wire support elements integrally formed from a single piece with the tubular body. The tubular body has a longitudinal central axis and a sealed lumen with a distal opening and a proximal opening. The wire support elements support an actuating wire. Each of the wire support elements has a feed-through opening receiving the actuating wire. A pair of adjacent wire support elements are separated from each other in an axial direction by a slot.

BRIEF DESCRIPTION OF THE DRAWINGS

The invention will now be described by way of example with reference to the accompanying Figures, of which:

FIG. 1 is a perspective view of a shaft according to an embodiment;

FIG. 2 is a detail perspective view of the shaft of FIG. 1;

FIG. 3 is a front view of the shaft of FIG. 1;

FIG. 4 is a side view of the shaft of FIG. 1;

FIG. 5 is another side view of the shaft of FIG. 1;

FIG. 6 is a sectional end view of the shaft, taken along line VI-VI of FIG. 5;

FIG. 7 is a sectional end view of the shaft, taken along line VII-VII of FIG. 5;

FIG. 8 is a sectional side view of the shaft, taken along line VIII-VIII of FIG. 5.

DETAILED DESCRIPTION OF THE EMBODIMENT(S)

Figure 9:
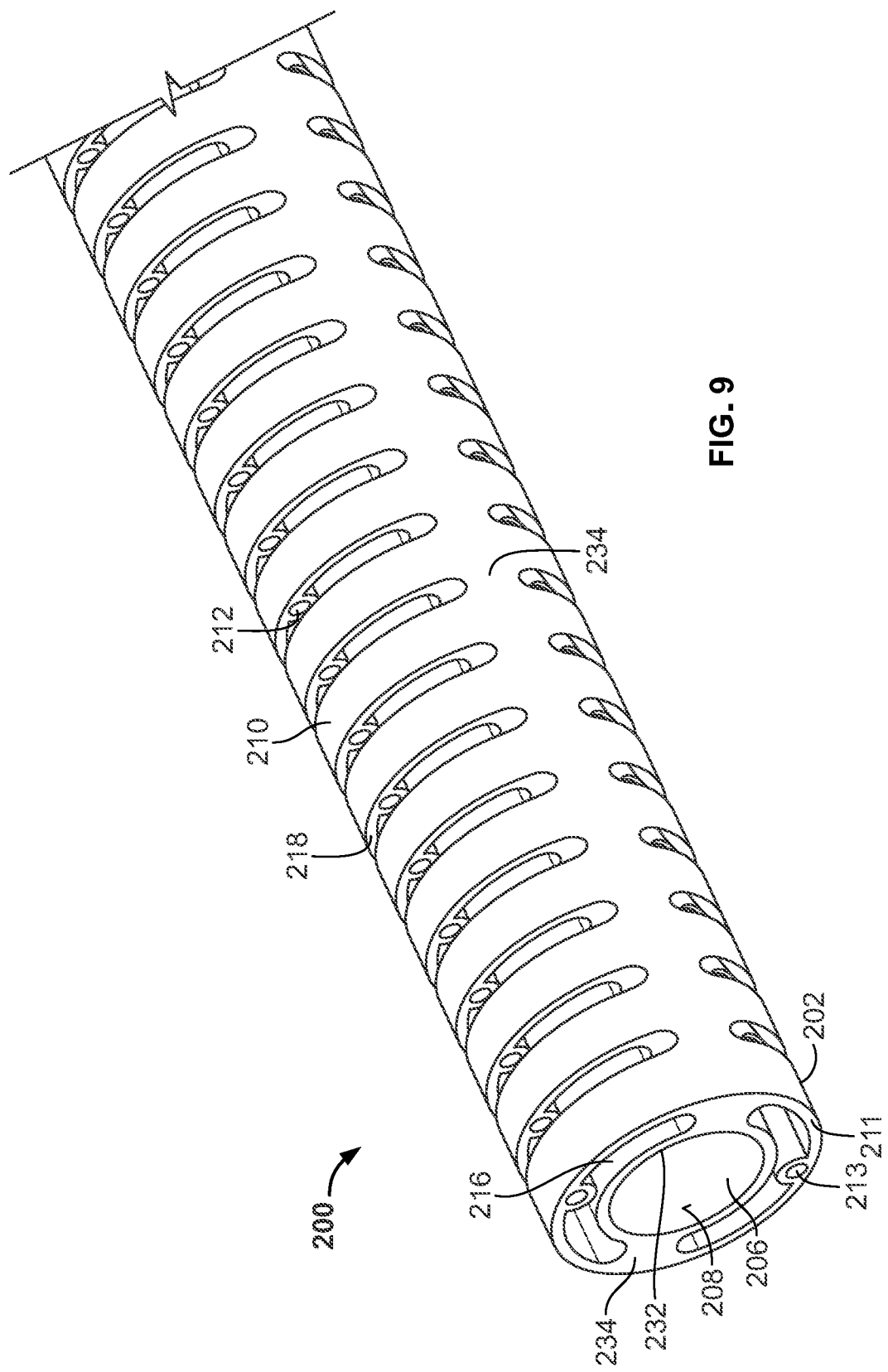
FIG. 9 is a perspective view of a shaft according to another embodiment.

The accompanying drawings are incorporated into the specification and form a part of the specification to illustrate several embodiments of the present invention. These drawings, together with the description, serve to explain the principles of the invention. The drawings are merely for the purpose of illustrating examples of how the invention can be made and used, and are not to be construed as limiting the invention to only the illustrated and described embodiments. Furthermore, several aspects of the embodiments may form—individually or in different combinations—solutions according to the present invention. The following described embodiments thus can be considered either alone or in an arbitrary combination thereof. Further features and advantages will become apparent from the following more particular description of the various embodiments of the invention, as illustrated in the accompanying drawings, in which like references refer to like elements.

An articulating shaft 100 according to an embodiment is shown in FIGS. 1 and 2. The shaft 100 has a distal end 102 with a distal opening and a proximal end 104 with a proximal opening. As used herein, the terms "proximal" and "distal" are to be taken as relative to a user using the disclosed delivery devices. "Proximal" is to be understood as relatively closer to the user and "distal" is to be understood as relatively farther away from the user.

The shaft 100 has a tubular body with a longitudinal central axis 130, the tubular body having at least one sealed, i. e. radially closed lumen with a distal opening and a proximal opening. A main lumen 106 extends along the complete length of the shaft 100, as shown in FIGS. 1 and 2. According to the present invention, the main lumen 106 is delimited by an inner wall, which is closed along the length of the shaft 100. Thus, the main lumen 106 can be sealed hermetically by connecting the distal and proximal ends 102, 104 to respective sealed fittings or connectors. The articulating shaft 100 for a steerable catheter is formed as one single piece, so that the main lumen 106 for inserting the catheter is completely sealed along the entire length of the shaft 100, 200. The main lumen 106, 206 may also be referred to as the "central lumen" or "core lumen".

According to the example shown in FIG. 1, the articulating shaft 100 has a plurality of wire support elements 110 each having at least one feed-through opening 112. The feed-through openings 112 are linearly arranged in the longitudinal direction of the shaft 100, so that a segmented lumen for a steering wire that can steer the shaft 100 is formed. It should be noted that, in the drawings, the steering wires and other elements that are inserted into the various lumens are not shown. Each of the wire support elements 110 is formed as a bracket which is separated from a tubular body 114 of the shaft 100 by a void 116. In an embodiment, the bracket is shaped symmetric with respect to a mirror plane orthogonally intersecting the cross-section and the central longitudinal axis 130 of the shaft 100. In particular, the feed-through opening 112 may be arranged in the middle of the bracket. In the shown embodiment, the body of the shaft 100 and the wire support elements 110 are integrally formed in a single piece.

Slots 118 separate each of the brackets 110 from the adjacent one in the axial direction, as shown in FIGS. 1 and 2. These slots 118 facilitate the bending of the articulating shaft 100 if a pull wire is inserted into the row of feed-through openings 112 and exerts bending forces on the shaft 100. The presence of the voids 116 further enhances the flexibility and pliability of the shaft 100. The slots 118 may also be referred to as notches.

The shaft 100 according to the first example further comprises reinforcement lumens 120, shown in FIGS. 1 and 2, for receiving reinforcement bars or wires. These reinforcement wires may for instance be made from steel, Nitinol, or other suitable materials having some elastic properties. The reinforcement wires may also be referred to as the neutral axis support wires because they stabilize the segments formed by the slots 118 in their alignment and position. In the shown embodiment, two reinforcement lumens 120 are provided. It is clear for a person skilled in the art, however, that any other number of lumens 120 may also be provided. Further, also additional lumens for electrical cables or fluid channels can be provided.

When a tensile load is applied, an actuating wire shortens and causes the slots 118 to close, thereby causing the assembly to bend in the direction of the slots 118. The neutral axis support wires arranged in the reinforcement lumens 120 also bend in order to allow the assembly to move. The reinforcement wires also carry some articulation axial load and keep tension on the assembly, thereby preventing the segments from separating. In order to facilitate the bending, the reinforcement lumen 120 may be segmented by peripheral regions of the slots 118.

As shown in FIG. 1, at the proximal end 104 a fluidic connector 122 may be provided for a sealed connection to, for instance, a rigid part of a catheter or to a handle. Of course, also at the distal end 102 a similar fluidic connector may be provided. Thereby, a complete sealing of the main lumen 106 can be achieved. If the shaft 100 is intended to contain electric cables, the connector 122 may also comprise a device for forming an electrical connection.

In the shown example, the shaft 100 has an essentially circular outer contour. However, any other cross-sectional outline may also be chosen, for instance an oval or polygonal contour. As shown here, also all openings forming a lumen have a circular cross-section. This is not necessarily the case; any other suitable cross-section, e. g. oval or polygonal, may also be used.

In an embodiment, the articulating shaft 100 is formed as a 3D printed part, additively building up the part along the longitudinal axis 130 of the shaft 100. In an embodiment, the shaft 100 is 3D printed from a biocompatible material. 3D printing has become an increasingly cost effective and accurate technology for producing medical material. 3D printing is an additive manufacturing (AM) process defined as a process of joining materials to make objects from 3D model data, usually layer upon layer, as opposed to subtractive manufacturing methodologies, such as traditional machining. 3D printing can deliver parts of very sophisticated and complex geometries with no need of post-processing, built from custom-made materials and composites with near-zero material waste, while being applicable to a diversity of materials, including smart materials such as shape memory polymers and other stimulus-responsive materials, or biocompatible materials. Therefore, 3D printing is a technology that allows designers and engineers to create unique products that can be manufactured at low volumes in a cost-effective way. In the field of medical engineering, 3D printing even allows to produce the shafts custom made and adapted to specific patients.

A particularly high freedom of design with low cost can be achieved if the shaft 100 is fabricated by the 3D printing process. However, the shaft 100 may also be fabricated by an extrusion process or an injection molding process. These processes are advantageous for high-volume production at low cost.

In an embodiment, the shaft 100 is fabricated from a polymer material having a durometer in the range of 30 Shore A to 70 Shore A. In another embodiment, the polymer material may have a durometer in the range of 35 Shore A to 40 Shore A. For instance, polyamide is a possible material. However, the shaft 100 may also be fabricated from any other suitable material. A material with a relatively low hardness is desirable if low pulling forces and a soft surface are sought, a harder material is advantageous, if an enhanced stiffness is needed.

Further views of the articulating shaft 100 according to the example shown in FIGS. 1 and 2 are depicted in FIGS. 3 to 8.

As may be derived from the frontal view of FIG. 3, the main lumen 106 has a center 128 which is offset with respect to a center 126 through which the longitudinal axis 130 of the shaft 100 is passing. Thus, more room can be given to the bracket 110 comprising the feed-through opening 112 and the pliability of the shaft 100 is enhanced. The first and second lumens 120 for the neutral axis support wires are arranged at the tubular body 114 in a way that they are directly opposing each other along a diameter leading through the center 126 of the shaft 100.

FIGS. 4 and 6 illustrate that the slots 118 which separate the plurality of segments formed by the wire support elements 110 from each other lead around the center 126 of the shaft 100 to cover a relatively large angle α of at least 45° and, in the shown embodiment, for instance 270°. Only a wall 132 forming the main lumen 106 remains closed continuously along the complete length of the shaft 100 for providing a sealed inner lumen 106. When the shaft is bent in a direction toward the feed-through openings 112, the slots 118 close, but also the brackets 110 formed by the voids 116 can be deformed if necessary, so that the distance between the feed-through openings 112 and the wall 132 is reduced. Thus, a sufficiently large segment of the shaft 100 has enough pliability to facilitate the steering process.

In an embodiment, each slot 118 may have a gradually diminishing depth in a radial direction towards the slot 118 peripheral regions around the circumference of the shaft 100. This design allows for an optimized force distribution when bending the shaft 100.

FIG. 9 illustrates a second embodiment of an articulating shaft 200 according to the present invention. The shaft 200 has a distal end 202 with a distal opening and a proximal end (not visible in this Figure) with a proximal opening.

A main lumen 206 extends along the complete length of the shaft 200 in the embodiment of FIG. 9. According to the present invention, the main lumen 206 is delimited by an inner wall 208, which is closed along the length of the shaft 200. Thus, the main lumen 206 can be sealed hermetically by connecting the distal and proximal ends to respective sealed fittings or connectors.

According to the example shown in FIG. 9, the articulating shaft 200 has a plurality of first wire support elements 210 each having a first feed-through opening 212 and a plurality of second wire support elements 211 each having a second feed-through opening 213. The feed-through openings 212, 213 are linearly arranged in the longitudinal direction of the shaft 200, so that two segmented lumens for two steering wires is formed. The rows of wire support elements 210, 211 are arranged opposite each other in a radial direction. Thus, a two way steerable catheter can be provided using the shaft 200 shown in FIG. 9. Again, it should be noted that in the drawings the steering wires and other elements that are inserted into the various lumens are not shown. Each of the wire support elements 210 is formed as a bracket which is separated from a tubular body 214 of the shaft 200 by a void 216.

Slots 218 separate each of the brackets 210 from the adjacent one, as shown in FIG. 9. These slots 218 facilitate the bending of the articulating shaft 200 if a pull wire is inserted into the row of feed-through openings 212, 213 and exerts bending forces on the shaft 200. The presence of the voids 216 further enhances the flexibility and pliability of the shaft 200.

The design of the shaft 200 further differs from the design of the shaft 100 in that the cross-section is symmetrical, in other words, that the center of the main lumen 206 is coaxial with the central axis of the shaft 200.

When the shaft 200 is bent in a direction towards one of the rows of feed-through openings 212, the notches 218 close, but also the brackets 210 formed by the voids 216 can be deformed if necessary, so that the distance between the feed-through openings 212 and the wall 232 is reduced.

In the embodiment shown in FIG. 9, each of the slots 218 extends along less than 180° of the outer circumference of the shaft 200, leaving two spines 234 for stabilizing the shaft 200. In the shown example, the spines 234 as such stabilize the neutral axis. However, it is clear for a person skilled in the art that one or more additional reinforcement lumens (similar to the ones shown with the first example of the shaft 100) can be embedded in the spines 234 for receiving a neutral axis support wire of bar. These reinforcement wires may for instance be made from steel, Nitinol, or other suitable materials having some elastic properties. The reinforcement wires may also be referred to as the neutral axis support wires because they stabilize the segments formed by the slots 218 in their alignment and position. When a tensile load is applied, the actuating wire on the respective side shortens and causes the notches 218 on the side of the actuated wire to close, thereby causing the assembly to bend in the direction of those notches 218. The neutral axis support wires arranged in the reinforcement lumens would also bend in order to allow the assembly to move. The reinforcement wires also carry some articulation axial load and keep tension on the assembly, thereby preventing the segments from separating. Further, also additional lumens for electrical cables or fluid channels can be provided. These lumens can be attached to the inner surface of the outer unsealed wall or they can be attached to the outer surface of the inner sealed wall.

Although not visible in FIG. 9, at the proximal end of the shaft 200 a fluidic connector may be provided for a sealed connection to for instance a rigid part of a catheter or to a handle. Of course, also at the distal end 202, a similar fluidic connector may be provided. Thereby, a complete sealing of the main lumen 206 can be achieved. If the shaft 200 is intended to contain electric cables, the connector may also comprise a device for forming an electrical connection.

In the shown example, the shaft 200 has an essentially circular outer contour. However, any other cross-sectional outline may also be chosen, for instance an oval or polygonal contour. As shown here, also all openings forming a lumen have a circular cross-section. This is not necessarily the case; any other suitable cross-section, e. g. oval or polygonal, may also be used.

In an embodiment, the articulating shaft 200 is formed as a 3D printed part, additively building up the part along the longitudinal axis of the shaft 200. However, it is clear that also other techniques of manufacturing the shaft 200 can be used. 3D printing is used to achieve the features required to allow articulation while also maintaining a sealed lumen.

In summary, the present invention may provide an articulating shaft 100, 200 design based on 3D printed low durometer biocompatible material, containing a sealed main lumen 106, 206. The 3D printed articulating design may contain one or more lumens for wires or cables and the sealed lumen 106, 206 may be placed concentric to the outer diameter or offset from the center axis. The outer wall contains notches 118, 218 to allow the shaft 100, 200 to contract and bend on this side.

In case of a two-way steering shaft 200, as shown in FIG. 9, it is advantageous to arrange the closed main lumen 206 concentrically within the outline of the shaft 200. On the other hand, for an articulating shaft 100 as shown in the embodiment of FIGS. 1 to 8, which has to be bent only in one direction, it is advantageous to arrange the main lumen 106 offset from the central axis 130, so that the closed lumen 106 is arranged within the outline of the shaft 100 with its central axis 128 being distanced from the longitudinal central axis 130 of the shaft 100. In this case, a larger part of the shaft's cross-section can be used for the wire support elements 110.

The wire or cable lumens can be attached to the inner surface of the outer unsealed wall or they can be attached to the outer surface of the inner sealed wall. Additional wires may be assembled into these lumens. These can be steel or Nitinol or other suitable materials with some elastic properties. These will be referred to as the neutral axis support wires. When these wires are attached to the distal end 102, 202 of the assembly and a tensile load applied then the wire (cable) shortens. This causes the notches 118, 218 to close, causing the assembly to bend in the direction of the notches 118, 218. The neutral axis support wires bend to allow the assembly to bend. These wires also carry some articulation axial load. The wires keep the segments 110, 210 in alignment and position. The wires also keep tension on the assembly, preventing the segments 110, 210 from separating. The notches 118, 218 can be configured in a multitude of ways, with single way and two way steering possible.

A hermetic sealing of the core lumen 106, 206 can be achieved easily without additional covers or sheaths. Moreover, the assembly process is facilitated due to the one-piece design of the shaft 100, 200.

The present invention further relates to a method for fabricating a shaft 100, 200 for a steerable catheter system, using 3D printing to achieve the features required to allow articulation while also maintaining a sealed lumen 106, 206. The method includes providing a tubular body with a longitudinal central axis, the tubular body having at least one closed lumen 106, 206 with a distal opening 102, 202 and a proximal opening 104. The method includes fabricating a plurality of wire support elements 110, 210, 211 for supporting at least one actuating wire, wherein each of the wire support elements 110, 210, 211 has at least one feed-through opening 112, 212, 213 for receiving the actuating wire, wherein two adjacent wire support elements 110, 210, 211 are separated from each other in an axial direction by a slot 118, 218, and wherein the body 114, 214 and the wire support elements 110, 210, 211 are integrally formed from a single piece.

What is claimed is:

1. An articulating shaft for a steerable catheter system, comprising:
   a tubular body having a longitudinal central axis and a radially sealed lumen with a distal opening and a proximal opening; and
   a plurality of wire support elements integrally formed from a single piece with the tubular body and supporting an actuating wire, each of the wire support elements has a feed-through opening receiving the actuating wire, a pair of adjacent wire support elements of the plurality of wire support elements are separated from each other in an axial direction by a slot, each of the wire support elements has a bracket separated from the tubular body by a void, the feed-through opening is arranged at the bracket and the void is positioned between the feed-through opening and the radially sealed lumen in a radial direction.

2. The articulating shaft of claim 1, wherein the slot extends by at least 45° in the radial direction around the tubular body.

3. The articulating shaft of claim 1, wherein the plurality of wire support elements include a first row of wire support elements and a second row of wire support elements extending along the longitudinal central axis, the first row and the second row are arranged opposite to one another in the radial direction.

4. The articulating shaft of claim 3, wherein the feed-through openings in the first row are aligned opposite to the feed-through openings in the second row.

5. The articulating shaft of claim 1, wherein the shaft has a circular radial outline.

6. The articulating shaft of claim 5, wherein the radially sealed lumen is arranged concentrically with the circular radial outline of the shaft.

7. The articulating shaft of claim 5, wherein the radially sealed lumen is arranged within the circular radial outline with a central axis of the radially sealed lumen distanced from the longitudinal central axis.

8. The articulating shaft of claim 1, wherein the shaft is formed from a 3D printed biocompatible material.

9. The articulating shaft of claim 1, further comprising a reinforcement lumen receiving a reinforcing wire.

10. The articulating shaft of claim 9, wherein the reinforcement lumen is segmented by the slot.

* * * * *